United States Patent
Corbett

(10) Patent No.: US 6,953,130 B2
(45) Date of Patent: Oct. 11, 2005

(54) GLOVE DISPENSER

(75) Inventor: Adrian Corbett, San Diego, CA (US)

(73) Assignee: Glove Box, Inc., Las Vegas, NV (US)

( * ) Notice: Subject to any disclaimer, the term of this patent is extended or adjusted under 35 U.S.C. 154(b) by 0 days.

(21) Appl. No.: 10/115,327

(22) Filed: Apr. 2, 2002

(65) Prior Publication Data

US 2002/0113079 A1 Aug. 22, 2002

Related U.S. Application Data

(63) Continuation-in-part of application No. 09/531,395, filed on Mar. 21, 2000, now abandoned.

(51) Int. Cl.$^7$ .............................................. B65M 3/00
(52) U.S. Cl. ........................... 221/191; 221/33; 221/45; 221/63
(58) Field of Search ............................ 221/191, 33, 45, 221/63, 30, 32, 38, 25; 223/11; 2/161.7

(56) References Cited

U.S. PATENT DOCUMENTS

| | | | | |
|---|---|---|---|---|
| 4,773,532 A | * | 9/1988 | Stephenson | 206/278 |
| 4,844,293 A | * | 7/1989 | McLaughlin | 221/34 |
| 4,909,413 A | * | 3/1990 | McCutcheon | 221/1 |
| 4,915,272 A | * | 4/1990 | Vlock | 223/111 |
| 5,803,245 A | * | 9/1998 | Wood | 206/69 |
| 5,816,440 A | * | 10/1998 | Shields et al. | 221/45 |
| 5,896,983 A | * | 4/1999 | Wood | 206/69 |
| 5,921,434 A | * | 7/1999 | Hollander et al. | 221/34 |
| 5,927,543 A | * | 7/1999 | Dejardi et al. | 221/56 |
| 5,934,462 A | * | 8/1999 | Gregory | 206/278 |
| 6,021,919 A | * | 2/2000 | Kelly | 221/25 |
| 6,053,380 A | * | 4/2000 | Sherrod | 223/111 |
| 6,708,841 B2 | * | 3/2004 | Baughman | 221/46 |
| 6,820,753 B2 | * | 11/2004 | Kurtz et al. | 211/53 |

* cited by examiner

Primary Examiner—Donald P. Walsh
Assistant Examiner—Michael Butler
(74) Attorney, Agent, or Firm—Steins & Associates, P.C.

(57) ABSTRACT

An Improved Glove Dispenser is disclosed. The disclosed dispenser will automatically open a pair of standard disposable gloves in response to a user request, preferably by voice. The dispenser further includes a shuttle assembly that will retrieve and position a pair of gloves for donning. The preferred dispenser will accept glove cartridges that can be loaded into the dispenser without being touched by the hands of the person installing the cartridges. In other embodiments of the disclosed dispenser, there is the capability to provide two or more different-sized or configured gloves for donning by users. The preferred dispenser further includes an embodiment whereby the gloves are inflated prior to being donned, in order to further assist the user in donning the gloves. The preferred dispenser further includes a glove donning rack assembly that has a unique glove release assembly for releasing gloves onto hands inserted into them when desired.

20 Claims, 10 Drawing Sheets

US 6,953,130 B2

GLOVE DISPENSER

This application is a continuation of application Ser. No. 09/531,395, filed Mar. 21, 2000, now abandoned.

BACKGROUND OF THE INVENTION

1. Field of the Invention

This invention relates generally to disposable sanitary gloves and, more specifically, to an Improved Glove Dispenser

2. Description of Related Art

Individuals in the health care industry regularly don disposable sterilized gloves in order to prevent the transmission of bacteria or other contaminants to themselves and to others. It is typical for these gloves to be dispensed from a common cardboard box similar to those used to dispense disposable facial tissues. In order to don a pair of gloves, the individual typically grabs a glove and pulls it from the box using an uncovered hand. Using one ungloved hand, the user slips the glove on to the other hand, after which the gloved hand is used to grab the second glove from the box and then to don it upon the ungloved hand. If we analyze the steps in this process, we can see that while the gloves originally started out being clean and antiseptic, by the time they are actually on the user's hand, they are likely to be anything but clean. In particular, the current (widely used) method requires that the exterior of the first glove and the glove dispenser be touched by ungloved hands. As such, the first glove donned can no longer be expected to be sanitary. Furthermore, the user then uses this potentially soiled glove to grab the second glove in order to don it. It is not a stretch to believe that both gloves are no longer sterile and clean.

A Nosocomial infection is any infection acquired while one is in the hospital. Nosocomial infections can be transmitted from person to person by health care workers who do not wash their hands properly between treating patients or by improper procedures, such as inadequate disinfection or sterilization of equipment. Approximately 2.4 million such infections occur each year in the United States, directly causing about 30,000 deaths and contributing to nearly 70,000 deaths annually. Hospital patients are particularly susceptible to nosocomial infections because their immune systems are often suppressed or compromised due to age, immunosuppresive medication, or other underlying causes, such as acquired immune deficiency syndrome (AIDS). Nosocomial infections, which progress rapidly and are frequently resistant to antibiotics, generally involve bacteria such as *Staphylococcus, Enterobacter*, or *Pseudomonas* or fungi such as *Candida*. In addition, some microorganisms that reside in a person's body and that normally cause little or no harm may start a nosocomial infection if the individual is treated with an antibiotic that destroys beneficial organisms, thus allowing disease-causing organisms to take over. These staff infections in particular are believed to be transmitted easily between the faces and the hands of human beings, and as such, would be easily transmitted in the aforementioned glove-donning process.

What is needed is a system that permits a user to don sanitary gloves without the need for them to first touch the outside of these gloves. In this way, the gloves would remain sanitary, even through the donning process.

SUMMARY OF THE INVENTION

In light of the aforementioned problems associated with the prior devices, it is an object of the present invention to provide an Improved Glove Dispenser. The preferred dispenser will automatically open a pair of standard disposable gloves in response to a user request, preferably by voice. It is a further object that the dispenser include a shuttle assembly that will retrieve and position a pair of gloves for donning. It is a still further object that the dispenser accept glove cartridges that can be loaded into the dispenser without being touched by the hands of the person installing the cartridges. It is another object that embodiments of the dispenser include the ability to provide two or more different-sized or—configured gloves for donning by users. It is yet another object that the dispenser include a glove donning rack assembly that further has a unique glove release assembly for releasing gloves onto hands inserted into them when desired. It is still another object that the dispenser include an embodiment whereby the gloves are inflated prior to being donned, in order to further assist the user in donning the gloves and reduce or even eliminate the need for powder in the gloves.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an Improved Glove Dispenser.

Figure 1:
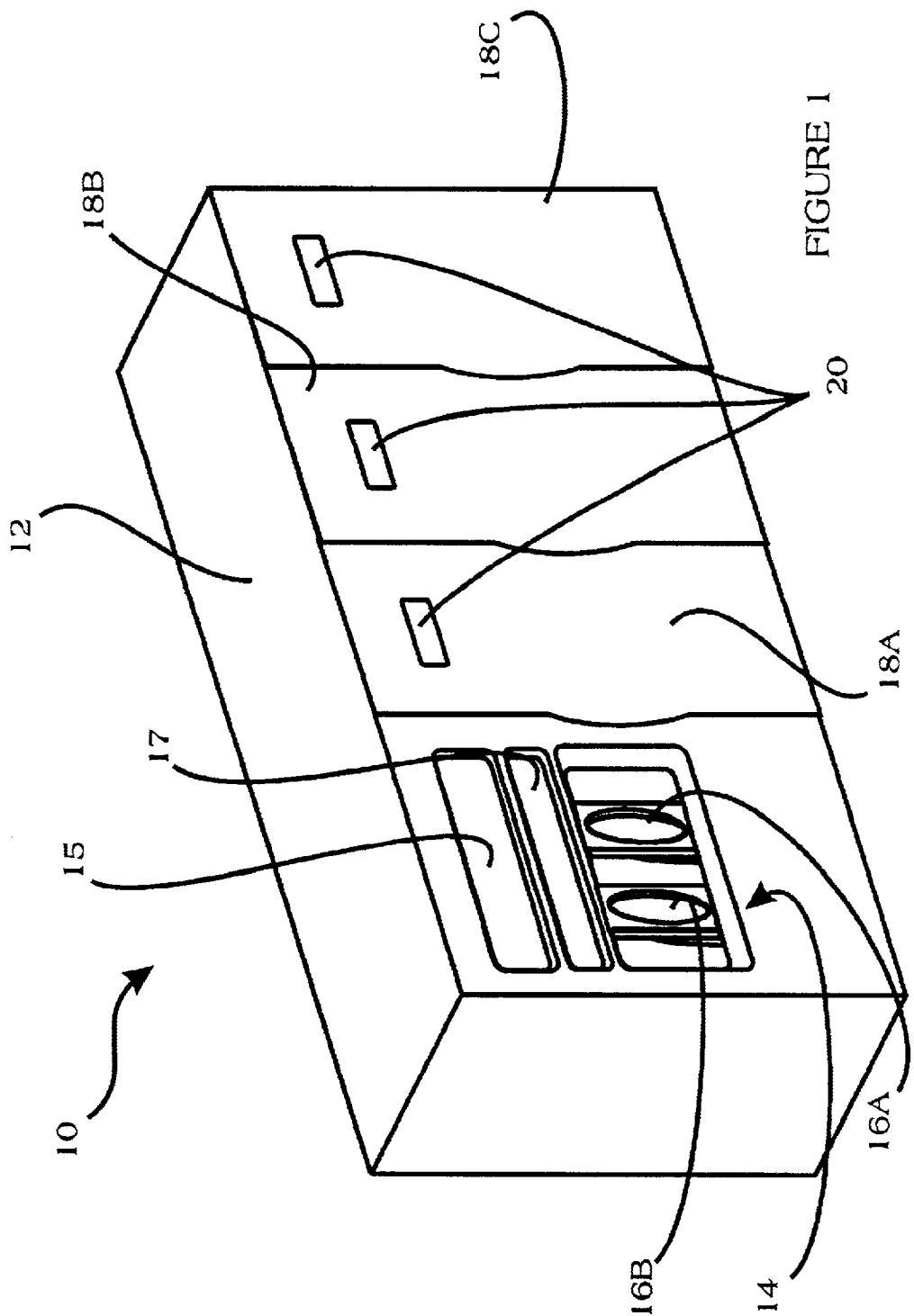
FIG. 1 is a perspective view of a preferred embodiment of the improved glove dispenser of the present invention.

The present invention can best be understood by initial consideration of FIG. 1. FIG. 1 is a perspective view of a preferred embodiment of the improved glove dispenser of the present invention. We see the Improved Glove Dispenser 10 currently comprises a housing 12 through which are formed one or more windows 14, behind which gloves 16A and 16B are mounted (for donning). The gloves 16A and 16B are provided for the user in such a way that the user need simply insert his or her hands through the window 14 in order to don the gloves 16A and 16B. In this way, the gloves are donned in a clean environment without the need for the user to touch the outside of them. Also formed in the housing 12 are plurality of doors 18A, 18B, and 18C. In its preferred form, each door 18 will also include an aperture 20; these apertures will be discussed more fully later, but essentially they provide the user with the ability to observe what size or style of glove is held behind each door 18. Still further, the device 10 may include one or more display screens 15 for displaying pertinent information for viewing by the user. For example, the screen 15 might instruct the user to speak certain words in order to activate the glove loading process. The screen might also provide functional status indication and even touch-sensitive switches represented thereon for operation of the unit 10.

Still further, one or more viewing apertures 17 might be formed in the housing 12, adjacent to the window 14. If, as depicted here, a viewing aperture 17 is above the window 14, the user can peer through the aperture 17 while the gloves are being donned. The aperture 17, therefore, will provide the user with additional dexterity and control during (and probably comfort) with the improved donning process. Now turning to FIG. 2, we can explore the present invention more fully.

Figure 2:
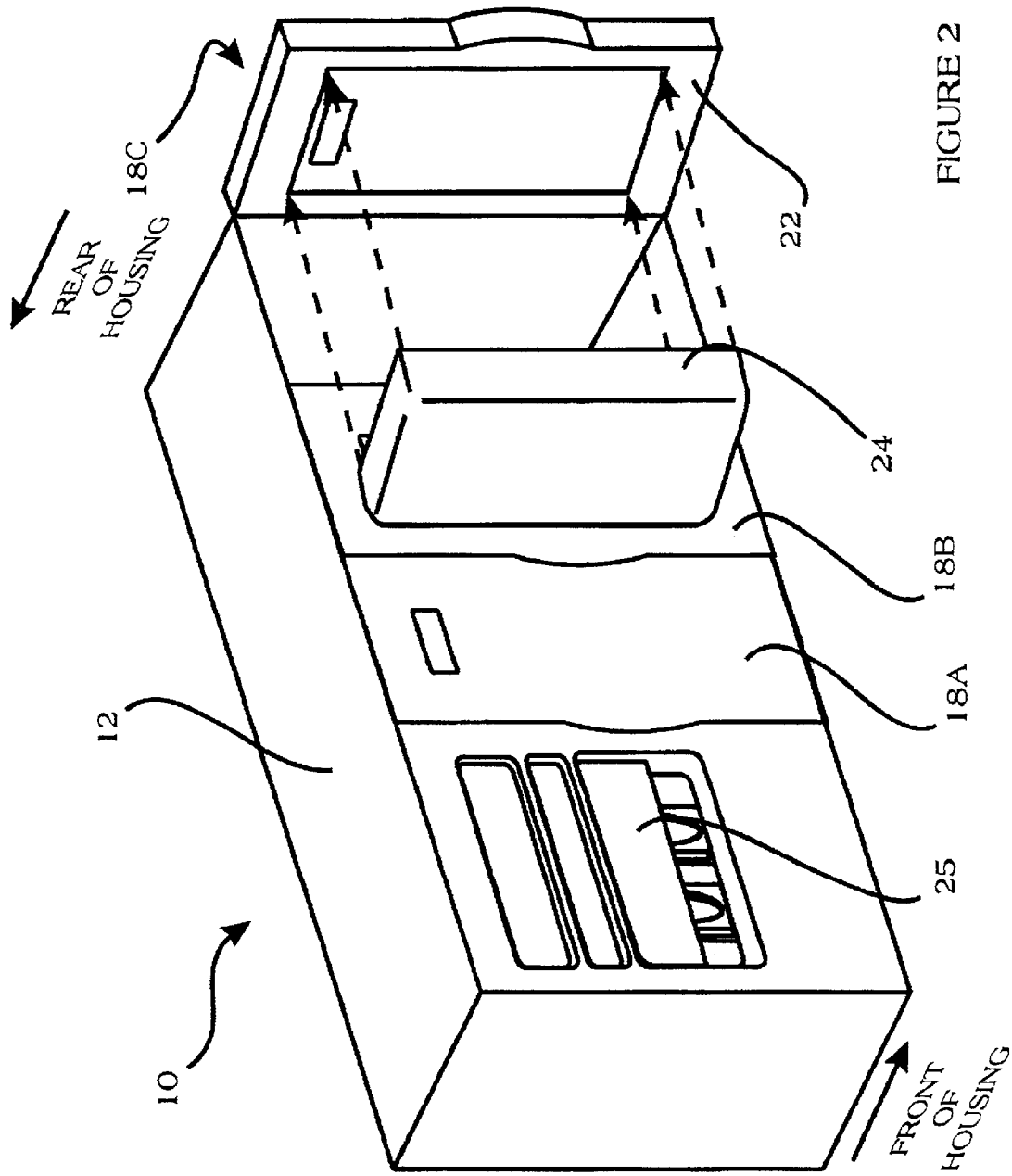
FIG. 2 is a perspective view of the dispenser of FIG. 1 depicting a glove cartridge loading method.

FIG. 2 is a perspective view of the dispenser of FIG. 1 depicting a glove cartridge 24 loading method. As can be seen here, the door 18C has been opened to reveal an inner surface 22 to which a glove cartridge 24 can be attached. It should be obvious that the glove cartridge 24 includes a label depicting the size of gloves attached to there, such that it might be viewed through the apertures (see FIG. 1) by the user. It should be appreciated that in the present embodiment of the dispenser 10, there are three doors (18A, 18B, and 18C) provided, in order that three different sizes of gloves might be installed within the housing 12 to provide a variety of different gloves. In other embodiments, there may be only two doors 18 or even a single door 18 version; depending on the particular application involved. Furthermore it should be understood that whoever is stocking the dispenser 10 with gloves has the choice of loading whatever sizes are most desirable for the environment.

In another (non-depicted) embodiment, the glove cartridge 24 will actually be inserted directly into the housing 12 through an opened door 18 (i.e. rather than being attached to the inside surface of the door 18). In either embodiment, the device 10 may include a feature of being able to determine what type of cartridge (e.g. glove size, glove type, etc.) is inserted into the housing 12 (or attached to the door 18) by interpreting a feature on the cartridge 24 itself. For example, the cartridge 24 may include a protrusion on its surface that is readable by the device 10 to indicate a particular feature of the gloves; another example includes the inclusion of an electronic data storage device/chip embedded into the cartridge 24 that can be read by the logic systems incorporated within the device 10.

Also depicted in FIG. 2 is the cover 25. In the present embodiment, the cover 25 shall preferably open and close in response to the donning of gloves. In the closed position, the window 14 will be covered (and possibly sealed) to prevent contamination to the inner workings of the device 10. The cover 25 shall open prior to the user inserting his or her hands into the gloves, and thereafter shall close once the hands have been removed. If we now turn to FIG. 3, we can further explore the benefits of the present invention.

Figure 3:
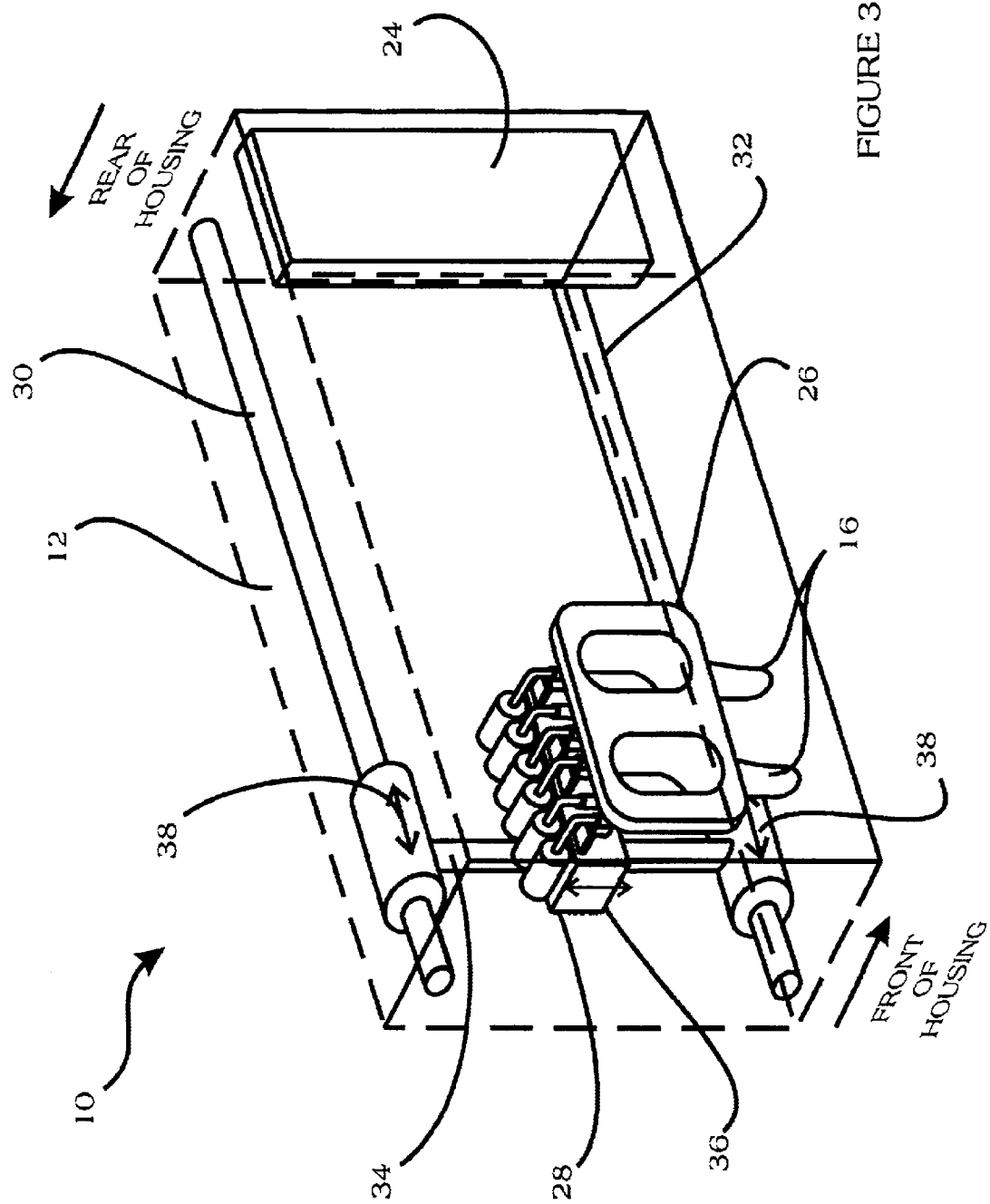
FIG. 3 is a perspective view of internal components of the dispenser of FIGS. 1 and 2.

FIG. 3 is a perspective view of internal components of the dispenser 10 of FIGS. 1 and 2. Within the housing 12, we can see the glove cartridge 24 and a glove donning rack assembly 26. The glove donning rack assembly is, very simply, a location for a pair of gloves 16 to be attached, and through which the user might don them. A further unique aspect of the present invention is how the gloves 16 are transferred from the cartridge 24 to the rack assembly 26; this step is accomplished by a shuttle assembly 28. The shuttle assembly 28 is preferably mounted within the dispenser 10 on an upper rail 30, a lower rail 32 and a vertical rail 34. In such a manner the shuttle assembly 28 can travel both on vertical path 36 and on horizontal paths 38 such that it can transit around the entire interior of the housing 12. The shuttle assembly 28 will be more fully described below in connection with later figures. If we now turn to FIG. 4 we can study the relationship between the glove cartridge 24 and the shuttle assembly 28.

Figure 4:
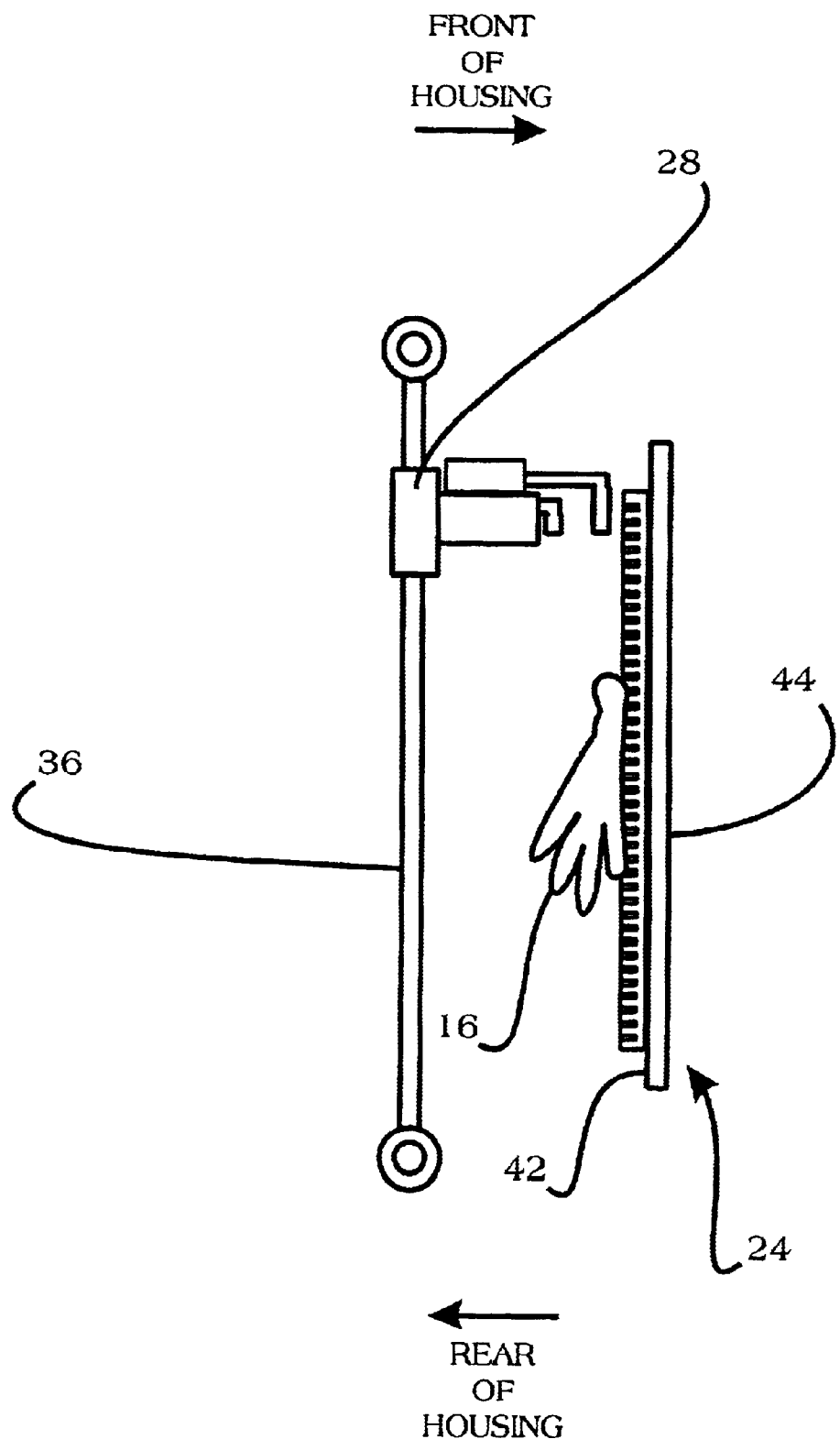
FIG. 4 is a cutaway side view of the shuttle assembly and cartridge designs of the dispenser of FIGS. 1 through 3.

FIG. 4 is a cutaway side view of the shuttle assembly 28 and cartridge 24 designs of the dispenser of FIGS. 1 through 3. As can be seen, shuttle assembly 28 is configured to cooperate with the glove cartridge 24 to remove gloves 16 therefrom. As can further be seen in this example, it is possible to attach a series of gloves 16 to a glove mounting means 40 that extends from the face 42 of the cartridge base 44. As will be discussed more fully below, the gloves 16 are removed from the glove mounting means 40 by a plurality of manipulative finger assemblies 60 extending from the facing side of the shuttle assembly. If we turn now to FIG. 5, we can examine exactly how this unique glove mounting means 40 operates.

Figure 5:
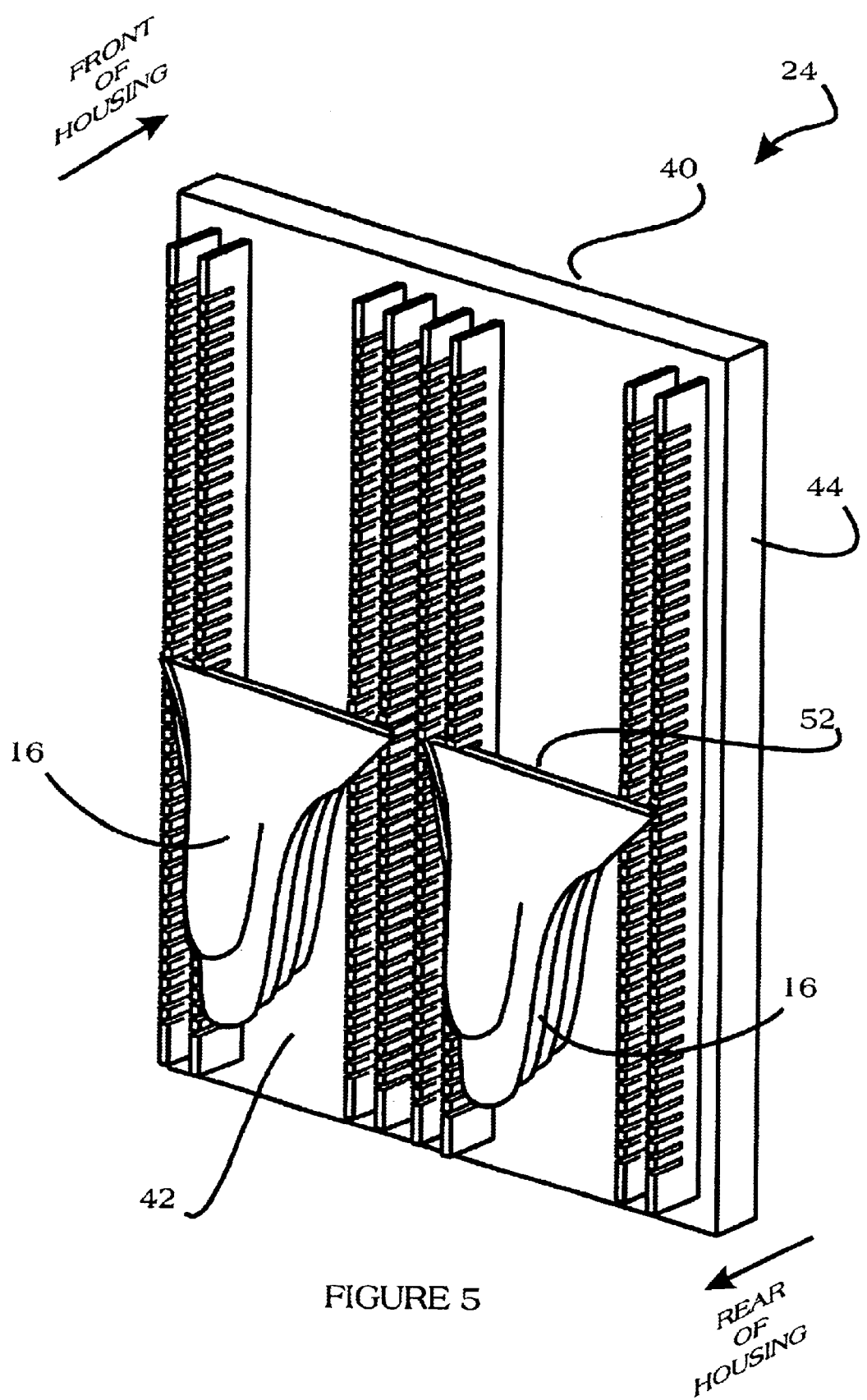
FIG. 5 is a perspective view of a glove cartridge of the dispenser of FIGS. 1 through 4.

FIG. 5 is a perspective view of a glove cartridge of the dispenser of FIGS. 1 through 4. As can been seen in FIG. 5, glove mounting means 40 are dispersed across the face 42 of the cartridge 24. Each mounting means 40 preferably comprises two pair of crimping rails 62, respectively arranged in spaced relation. The rails 62 are provided to removably hold the cuffs 52 of the gloves 16 hanging from the base 44. In this embodiment, the rails 62 include a plurality of notches cut into their edges; the cuffs 52 are easily pressed into, and pulled out of these notches. Although not shown here, it should be understood that the cartridge 24 (including a full load of gloves 16) is sealed by a sterile or sanitary (and disposable) casing or sheet. In another (non-depicted) embodiment, the cuffs 52 might actually be lightly glued or otherwise adhered to the face 42 or the cartridge 24 (for example to the rails 62); the choice of attachment means is one of manufacturing cost and convenience. We will now turn to FIG. 6 and discuss the operation of the shuttle assembly 28.

Figure 6:
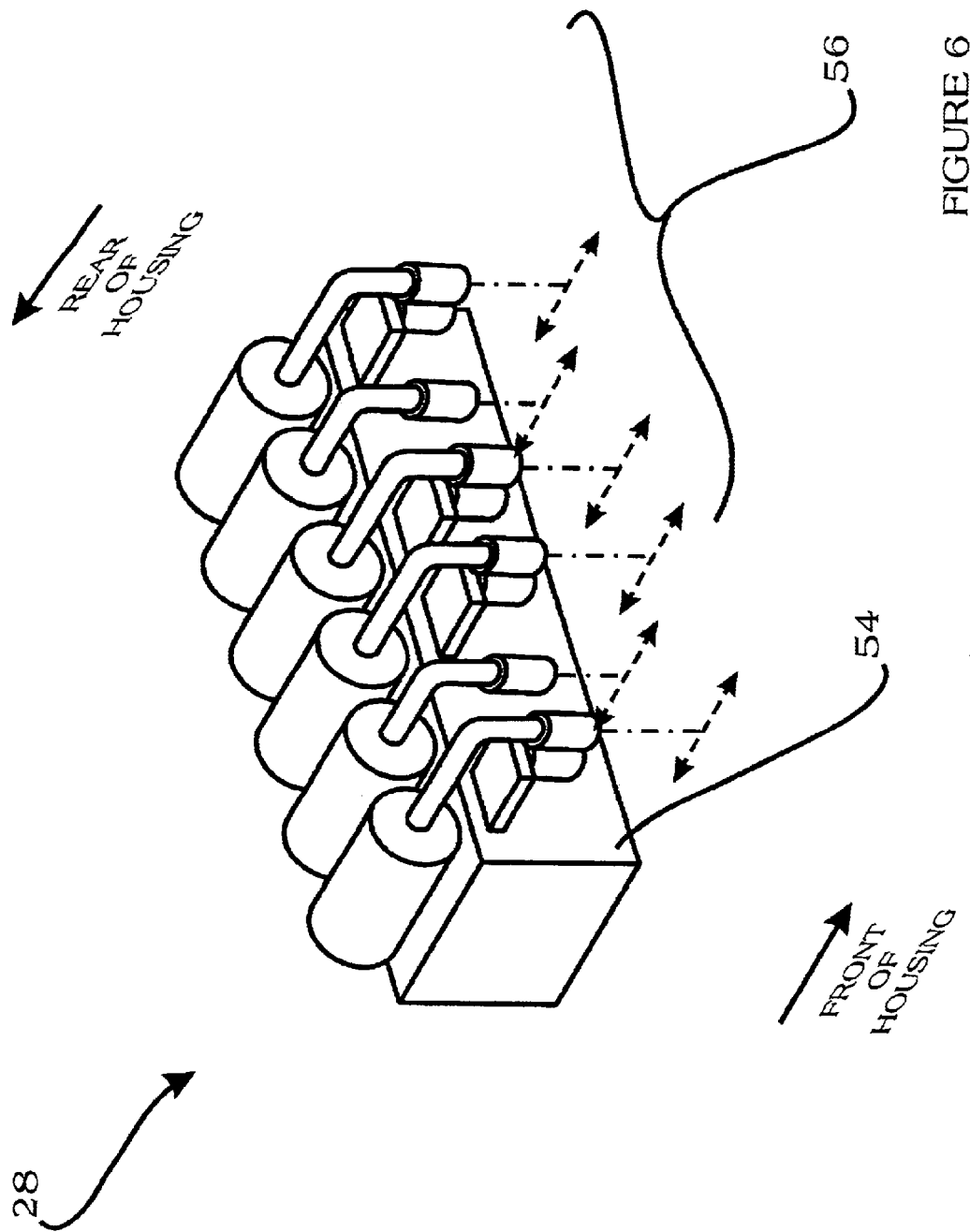
FIG. 6 is a preferred embodiment of the shuttle assembly of the dispenser of FIGS. 1 through 5.

FIG. 6 is a preferred embodiment of the shuttle assembly 28 of the dispenser 10 of FIGS. 1 through 5. It can be seen that the preferred shuttle assembly 28 comprises a housing 54, from which preferably extends a plurality of finger assemblies 56 (two shown here). Each finger assembly 56 comprises one or more actuator(s) 68 from which a number of arms 70 extend. The actuators 68 control the arms 70 such that the tips 74 (and the arms 70 themselves) travel out and in, in the direction depicted by arrows 76. As further can be seen, the first arm 70A and third arm 70C are each paired with a stationary finger 72A and 72B, respectively. These moveable arm 70 and stationary finger 72 pairs provide a means for the assembly 28 to grasp the two sides of a glove (not shown). The arms 70 need simply move away from the stationary fingers 72 in order to release the pinching force being applied to the gloves (not shown).

In this embodiment, each finger assembly 56 further comprises a second arm 70B located between the first and third arms 70A and 70C, respectively. This center or second arm 70B is used to pull and release the center portion of the cuff of the glove (not shown), such as when stretching the gloves over the lip of the donning rack assembly (see below in connection with FIGS. 7 and 8). The actuators might be solenoid-operated-gear-operated-rams, or other well-known mechanisms for pushing and pulling the tips 74 with respect to the housing 54.

Once the gloves (not shown) are detached from the glove cartridge (not shown), the shuttle assembly transits to the glove donning rack assembly. It is at the glove donning rack assembly 26 that the gloves are released from the finger assembles 56 and placed upon glove donning rack assembly 26, as discussed below in connection with FIG. 7.

Figure 7:
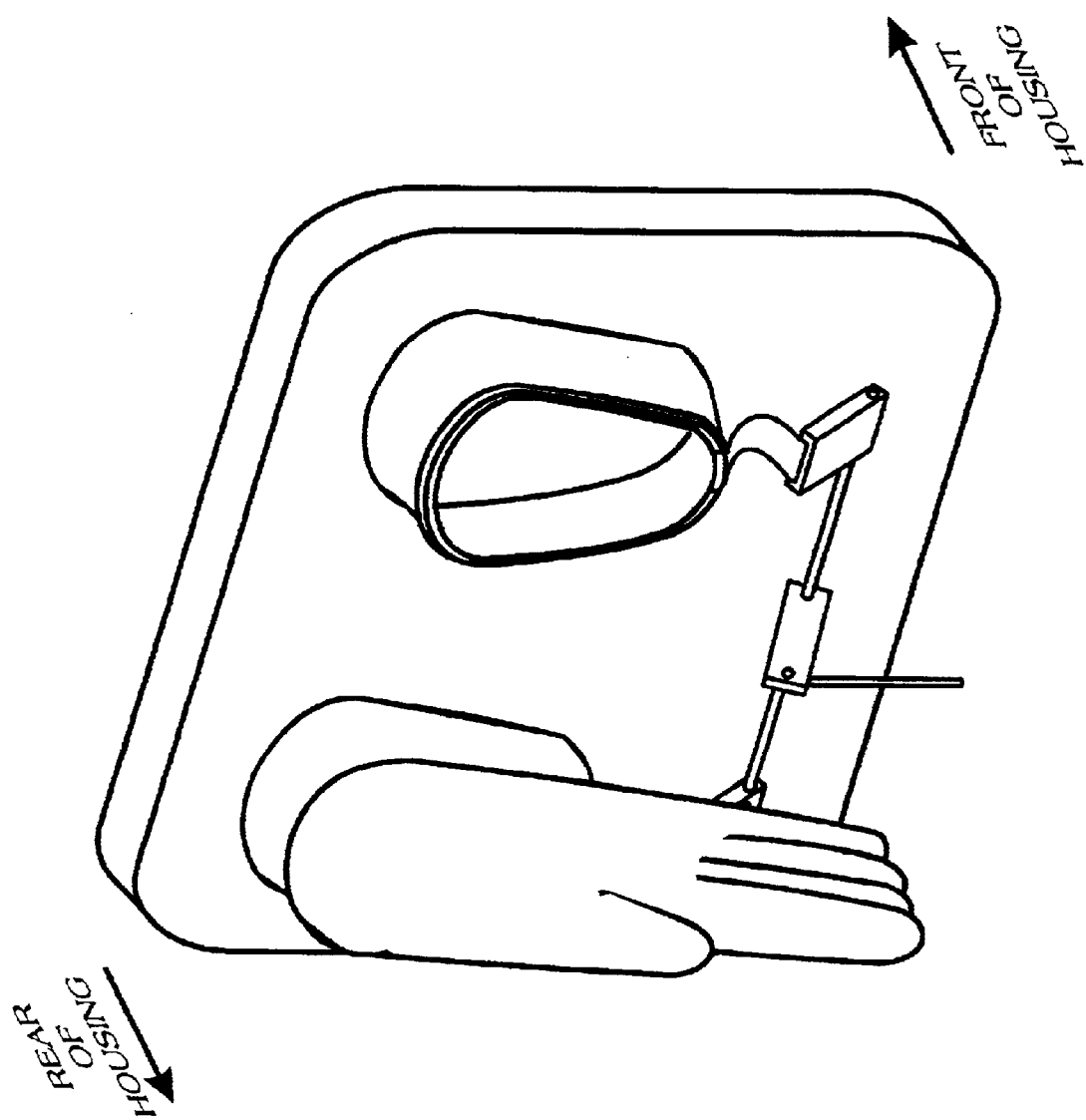
FIG. 7 is a preferred glove-donning rack assembly of the dispenser of FIGS. 1 through 6.

FIG. 7 is a preferred glove donning rack assembly 26 of the dispenser 10 of FIGS. 1 through 6. The preferred donning rack assembly 26 comprises a base 64 that has a face 66 from which extend a pair of throats 78. The throats 78 terminate in an oblong rim 80, which is further defined by a underturned lip 82. The underturned lip 82 is generally provided in order to retain the cuff 52 of a glove 16 stretched over the end of the throat 78. As shown, the rim 80 forms the periphery of a window 68; it is through this window 68 that a user inserts their hand in order to don a glove 16 (that is stretched over the end of the throat 78).

Once the cuff 52 is securely held on the end of the throat 78 by the lip 82, it will not release its grip simply by inserting one's hand into the glove 16; additional release assistance is necessary—this is provided by the glove release assembly 84. The glove release assembly 84 comprises a first actuator linkage 88 for driving the end of a second actuator linkage 90, thereby translating translational motion to rotational motion. the second actuator linkage 90 then rotationally drives a shaft 86, which then causes a pair of third actuator linkages 92 to operate. From the distal end of each of the third actuator linkages 92, flexible strips 94 extend to the rim 80, where they are attached. Two things should be casually obvious from the depicted design: (1) when a glove 16 is stretched over the rim 80, the flexible strip 94 must be in a curved or slackened condition (as shown); and (2) if the third actuator linkage 92 is rotated so that the distal end is moving downwardly (in this depiction), then the flexible strip 94 will ultimately be taut. At or before the point that the flexible strip becomes taut, the portion of the cuff 52 overlapping the flexible strip 52 will be lifted off of the rim 80, cascadingly causing the rest of the cuff 52 to be released from the rim 80. If we now turn to FIGS. 8A and 8B, we can examine the operation of the glove release assembly 84, alone.

Figure 8B:
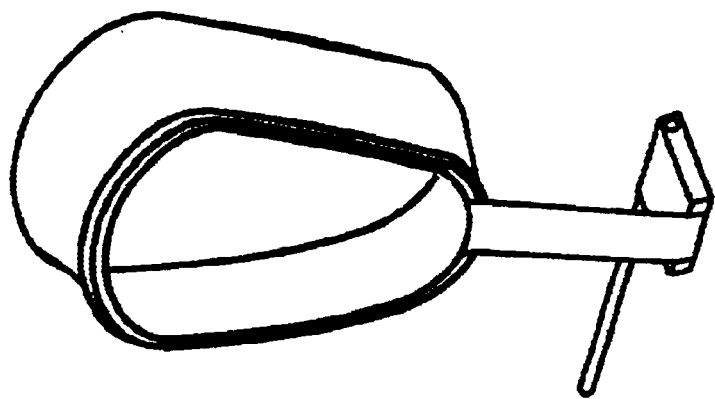
FIGS. 8A and 8B depict the operation of the glove release assembly of FIG. 7.
Figure 8A:
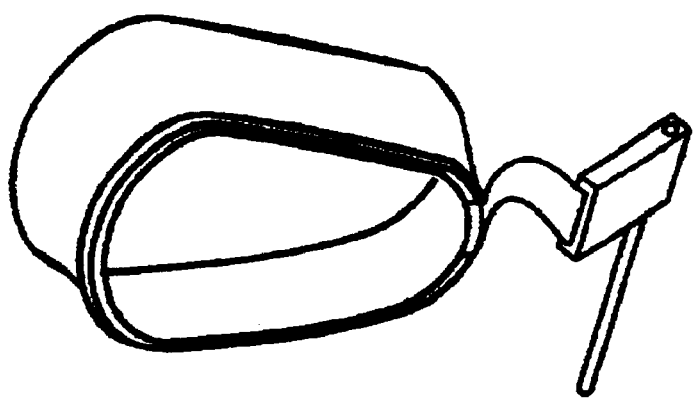

FIGS. 8A and 8B depict the operation of the glove release assembly of FIG. 7. In FIG. 8A, the flexible strip 94 is in the "idle," or "slackened" position; the glove release assembly 84 would be in this position prior to a glove (not shown) being stretched over the end of the throat 78. FIG. 8B depicts the glove release assembly 84 in the "release," or "taut" position, where the flexible sheet has been made taut in order to force that portion of the cuff of the glove (not shown) off of the lip 82, presumably after the user had inserted their hands into the gloves.

It is a simple matter, then, of the user removing his or her hands from the windows (see FIG. 1) with the newly gloved hands.

In a preferred embodiment, some actions of the shuttle assembly and glove donning rack assembly will be provided by stepper (or other suitable) motors. It is also preferred that the control of the apparatus be automated through employment of microprocessor, progammable logic controller or other electronic controller means. Still further, activation of the glove-providing process by the shuttle and glove donning rack assembly will preferably be by the user's voice, although push-button-activated systems (or hybrid systems) are also preferred embodiments.

An alternate embodiment of the glove dispenser of the present invention is also conceived. The device of the alternate embodiment adds the additional feature of inflation of the glove in order to facilitate the donning process; this device is first depicted in FIG. 9.

Figure 9:
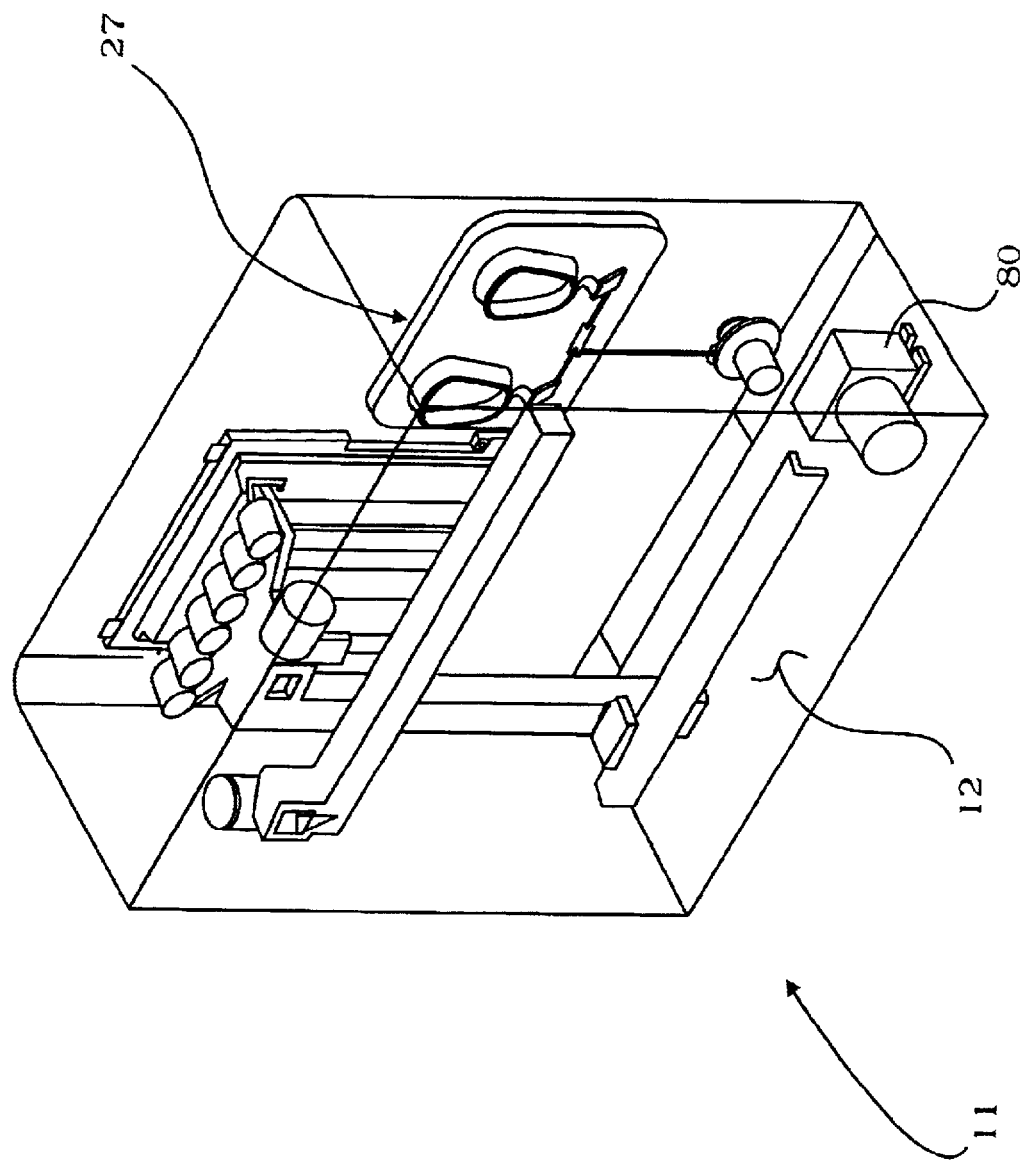
FIG. 9 is a cutaway perspective view of an alternative embodiment of the present invention that includes a vacuum glove inflation feature.

FIG. 9 is a cutaway perspective view of an alternative embodiment of the present invention 11 that includes a vacuum glove inflation feature. Within the housing 12 of this embodiment, there shall be found vacuum pump means 80 for drawing a vacuum on the chamber formed by the housing 12, such that the gloves that have been placed in position for donning and will inflate with ambient air. While an internal vacuum pump is shown here, it should be understood that the vacuum source may, in fact be external to the housing 12, in which case, a simple vacuum port will be needed opening to the chamber formed by the housing 12.

Figure 10:
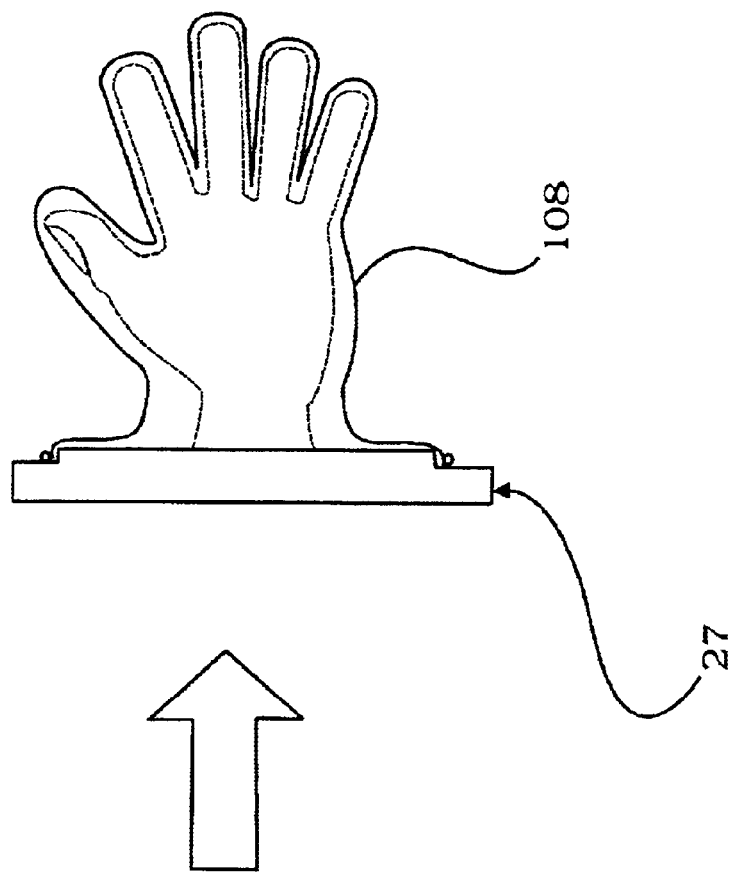
FIG. 10 is a side view of an individual's hand engaged in donning a glove via the preferred device.
Figure 10:
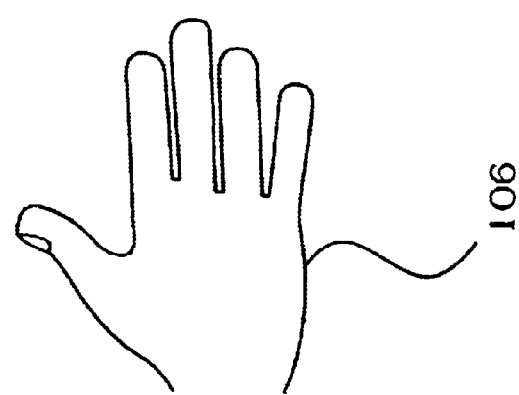

If we turn to FIG. 10, we can see a general depiction of how an individual would insert their hand into a glove inflated by the device of the present invention. It should be apparent that much of the structure of the present invention has been eliminated in the depiction of FIG. 10 for the purposes of clarity. As shown then, once the device 10 of the present invention has caused the glove to inflate 108, the force of the inflation will cause the glove to extend outwardly away from the glove donning rack assembly 27 (to which the glove is attached by its cuff). In this way, the open cuff of the glove will present a very simply conduit into which the user need simply insert his or her hand, as shown. Since the glove is inflated 108, the walls of the glove will not catch on the user's hand as he or she inserts the hand into the glove (unlike the prior donning methods).

Finally, it should be understood that one substantial benefit to the design of the present invention is the reduction in need for powdering of gloves. Powder is applied to the gloves to assist in the manual donning process; since it will now be much easier to don the gloves, less (or no) powder will be necessary. By reducing or eliminating the need for powdered gloves, there can be expected to be a reduction of both nosocomial infection as well as allergic reactions to the powder itself. Furthermore, even with eliminating the powder, it has been demonstrated that the time necessary to don a pair of gloves is reduced by at least 50% by the present system over the manual donning process.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A automated glove dispenser, comprising:
   a housing defined by a front side and an interior, and further having a pair of windows formed through said front side;
   at least one glove cartridge for attaching within said housing, each said glove cartridge including at least two gloves mounted thereon, and defined by two pair of crimping rails in spaced relation extending in spaced relation from a cartridge base, said crimping rails further defined by a plurality of notches, said notched provided for acceptance and retention of gloves thereon;

a shuttle assembly for removing said gloves from said cartridge and positioning them adjacent to said windows, said shuttle assembly responsive to audible command; and a glove donning rack assembly located within said interior adjacent to said windows and cooperating with said shuttle assembly to receive said gloves from said shuttle assembly.

2. The dispenser of claim 1, wherein:

said glove donning rack assembly is further defined by a face and a pair of throats extending therefrom and to which said gloves are transferable from said shuttle assembly.

3. An automated glove dispenser, comprising:

a housing defined by a front side and an interior, and further having a pair of windows formed through said front side;

at least one glove cartridge for attaching within said housing, each said glove cartridge including at least two gloves mounted thereon, and defined by two pair of crimping rails in spaced relation extending in spaced relation from a cartridge base, said crimping rails further defined by a plurality of notches, said notched provided for acceptance and retention of gloves thereon; and a shuttle assembly, said shuttle assembly configured to remove said gloves from said cartridge and positioning them adjacent to said windows, said shuttle assembly further comprising a shuttle housing and at least two finger assemblies extending from said housing and configured to cooperate with glove mounting means for mounting gloves on a face of said cartridge base.

4. The dispenser of claim 3, wherein said glove housing defines an interior, said dispenser further comprising a glove donning rack assembly located within said interior adjacent to said windows and cooperating with said shuttle to receive said gloves from said shuttle assembly.

5. The glove dispenser of claim 4, wherein said glove donning rack assembly comprises:

a rack base defined by a face; and a pair of throats extending from said face, each said throat terminating in a rim, said rims forming windows for inserting one's hands therethrough.

6. The glove dispenser of claim 5, wherein each said glove is further defined by a glove cuff, and said glove donning rack assembly further comprises:

a lip formed in aid rim for retining a glove cuff thereon.

7. The glove dispenser of claim 6, further defined by a glove release assembly cooperating with said glove donning rack assembly, said glove release assembly comprising;

a pair of rotatable actuator linkages further defined by distal ends; and flexible sheets extending from said distal ends to said rims.

8. The glove dispenser of claim 7, wherein each said finger assembly further comprises:

first, second and third arms, each said arms terminating in tips; and first, second and third actuators for causing said arms and tips to move axially.

9. The glove dispenser of claim 8, further including vacuum means, disposed in said housing, for creating a sub-atmospheric pressure condition in said chamber.

10. The glove dispenser of claim 3, wherein said glove mounting means comprise:

at least one pair of crimping rails spaced relation, said crimping rails further defined by a plurality of notches formed therein for acceptance of said gloves.

11. The glove dispenser of claim 3, further including vacuum means, disposed in said housing, for creating a sub-atmospheric pressure condition in said chamber.

12. The glove dispenser of claim 4, wherein said glove mounting means comprise:

at least one pair of crimping rails spaced relation, said crimping rails further defined by a plurality of notches formed therein for acceptance of said gloves.

13. The glove dispenser of claim 3, wherein said glove donning rack assembly comprises:

a rack base defined by a face; and a pair of throats extending from said face, each said throat terminating in a rim, said rims forming windows for inserting one's hands therethrough.

14. The glove dispenser of claim 13, wherein each said glove is further defined by a glove cuff, and said glove donning rack assembly further comprises:

a lip formed in said rim for retaining a glove cuff thereon.

15. The glove dispenser of claim 14, further defined by a glove release assembly cooperating with said glove donning rack assembly, said glove release assembly comprising:

a pair of rotatable actuator linkages further defined by distal ends; and flexible sheets extending from said distal ends to said rims.

16. The glove dispenser of claim 15, wherein each said finger assembly further comprises:

first, second and third arms, each said arms terminating in tips; and first, second and third actuators for causing said arms and tips to move axially.

17. The glove dispenser of claim 16, further including vacuum means, disposed in said housing, for creating a sub-atmospheric pressure condition in said chamber.

18. The glove dispenser of claim 2, wherein said glove donning rack assembly comprises:

a rack base defined by a face; and a pair of throats extending from said face, each said throat terminating in a rim, said rims forming windows for inserting one's hands therethrough.

19. The glove dispenser of claim 18, wherein each said glove is further defined by a glove cuff and said glove donning rack assembly further comprises:

a lip formed in said rim for retaining a glove cuff thereon.

20. The glove dispenser of claim 19, further defined by a glove release assembly cooperating with said glove donning rack assembly, said glove release assembly comprising:

a pair of rotatable actuator linkages further defined by distal ends; and flexible sheets extending from said distal ends to said rims.

* * * * *